US011308172B2

(12) United States Patent
Kim (10) Patent No.: US 11,308,172 B2
(45) Date of Patent: Apr. 19, 2022

(54) BIOLOGICAL SYSTEM INFORMATION RETRIEVAL SYSTEM AND METHOD THEREOF

(71) Applicant: Sun-Joong Kim, Daejeon (KR)

(72) Inventor: Sun-Joong Kim, Daejeon (KR)

(73) Assignee: Sun-Joong Kim, Daejeon (KR)

( * ) Notice: Subject to any disclaimer, the term of this patent is extended or adjusted under 35 U.S.C. 154(b) by 189 days.

(21) Appl. No.: 16/475,961

(22) PCT Filed: Jan. 8, 2018

(86) PCT No.: PCT/KR2018/000364
§ 371 (c)(1),
(2) Date: Jul. 3, 2019

(87) PCT Pub. No.: WO2018/128502
PCT Pub. Date: Jul. 12, 2018

(65) Prior Publication Data
US 2019/0332634 A1 Oct. 31, 2019

(30) Foreign Application Priority Data

Jan. 9, 2017 (KR) .......................... 10-2017-0003066

(51) Int. Cl.
*G06F 16/9532* (2019.01)
*G06F 16/9538* (2019.01)
(Continued)

(52) U.S. Cl.
CPC ...... *G06F 16/9532* (2019.01); *G06F 16/9538* (2019.01); *G16B 45/00* (2019.02); *G16B 50/00* (2019.02)

(58) Field of Classification Search
CPC . G06F 16/9532; G06F 16/9538; G16B 50/00; G16B 45/00
See application file for complete search history.

(56) References Cited

U.S. PATENT DOCUMENTS

| 9,679,030 B2* | 6/2017 | Hatami-Hanza | ........ G06F 16/22 |
| 2003/0009099 A1* | 1/2003 | Lett | ......................... G16B 50/00 |
| | | | 600/416 |
| 2020/0211692 A1* | 7/2020 | Kalafut | .................. G16H 30/20 |

FOREIGN PATENT DOCUMENTS

| KR | 10-2005-0060646 | 6/2005 |
| KR | 10-2012-0113736 | 10/2012 |

(Continued)

OTHER PUBLICATIONS

Andrew B Clegg et al.; benchmarking natural-language parsers for biological applications using dependency graphs; published Jan. 25, 2007 Jan. 2007 (Year: 2007).*

(Continued)

*Primary Examiner* — Anil K Bhargava
(74) *Attorney, Agent, or Firm* — IP & T Group LLP (57) ABSTRACT

Biological System information retrieval system and method thereof disclosed. The biological system information retrieval system may include a query inputting unit, configured for inputting a retrieval query being described to have at least one of a current state and an expected result, a query parsing unit, configured for extracting a token for the current state and the expected result from the retrieval query, and generating at least one of a first corpus data set for the current state and a second corpus data set for the expected result by using the token, and a retrieval requesting unit, configured for inputting at least one of the first corpus data set and the second corpus data set and an option value being generated according to a predetermined syntax to an information management device in order to retrieve a biological system information having similarity.

15 Claims, 5 Drawing Sheets

(51) Int. Cl.
 *G16B 45/00* (2019.01)
 *G16B 50/00* (2019.01)

(56) References Cited

FOREIGN PATENT DOCUMENTS

| KR | 10-1400946 | 5/2014 |
|----|------------|--------|
| KR | 10-2015-0125093 | 11/2015 |
| KR | 10-2016-0120583 | 10/2016 |

OTHER PUBLICATIONS

Lee T Sam et al.; an integrated resource for the multiscale mining of clinical and biological data; published Feb. 5, 2009 (Year: 2009).*

* cited by examiner

| | 1st biological system information | 2nd biological system information | 3rd biological system information | ... | nth biological system information |
|---|---|---|---|---|---|
| Corpus data set | Similarity index assessment value | Similarity index assessment value | Similarity index assessment value | | Similarity index assessment value |

FIG. 4B

| | 1st biological system information | 2nd biological system information | 3rd biological system information | ... | nth biological system information |
|---|---|---|---|---|---|
| Biological word | Similarity index assessment value | Similarity index assessment value | Similarity index assessment value | | Similarity index assessment value |

FIG. 5

BIOLOGICAL SYSTEM INFORMATION RETRIEVAL SYSTEM AND METHOD THEREOF

CROSS-REFERENCE TO RELATED APPLICATIONS

This application is a national stage application of PCT/KR2018/000364 filed on Jan. 8, 2018, which claims priority of Korean patent application number 10-2017-0003066 filed on Jan. 9, 2017. The disclosure of each of the foregoing applications is incorporated herein by reference in its entirety.

FIELD OF INVENTION

The present invention relates to a biological system information retrieval system and method thereof.

RELATED ART

Recently, an approach that enables a designer to extract or retrieve biological knowledge fast and precisely from explosively increasing documents in biology is required.

Through this approach, it will become possible to suggest a goal of effective development in various fields of technology such as developing a semi-permanent jointing method or IFF (identification of friend or foe) method for bio-inspired robot by use of biological knowledge.

But, the conventional retrieval algorithm for biological knowledge is remarkably poor at supporting a cognitive search process of designer.

Although bio information retrieval service accessible via Internet for providing comprehensive information related to organism such as gene sequence is partially implemented, it can provide information limited to biological relations of an organism but cannot provide an integrated retrieval for various information such as physical relations.

Besides, although a technique to extract relations between biological entities from biological structure documents by use of biological entity name, this technique is also based on information limited to biological relations of an organism.

As described above, conventional retrieval systems for biological knowledge can provide a keyword search for very narrow scope of information or a simple search result according to image matching.

SUMMARY

The present invention is for providing a biological system information retrieval system and method thereof that enable a designer in the bio-inspired design to conduct an effective retrieval by using various information and conditions, and to help the designer design inventively by implementing biological system information, which is subject of mimicking and applying in bio-inspired design, including physical relations, ecological relations and/or biological relations, as a comprehensive causal model, and constructing it by ontology.

Other advantages and objectives will be easily appreciated through description below.

According to one aspect of the present invention, a biological system information retrieval system is provided. The biological system information retrieval system may include a query inputting unit, configured for inputting a retrieval query being described to have at least one of a current state and an expected result, a query parsing unit, configured for extracting a token for the current state and the expected result from the retrieval query, and generating at least one of a first corpus data set for the current state and a second corpus data set for the expected result by using the token, and a retrieval requesting unit, configured for inputting at least one of the first corpus data set and the second corpus data set and an option value being generated according to a predetermined syntax to an information management device in order to retrieve a biological system information having similarity. The information management device may generate, store and manage the biological system information that is specified by physical relations, ecological relations, and biological relations for each organism.

The biological system information may be structured information in which nodes are indexed respectively with at least one term according to a predetermined syntax. The nodes may be CoS (Change of State) element, PPH (Physical Phenomena) element, PEF (Physical Effects) element, Input element, EPH (Ecological Phenomena) element, EBH (Ecological Behavior) element, Organ element, Part element, Entity element, and Action element.

The retrieval requesting unit may assess a similarity between the token of the corpus data set and a term indexed to correspond to the PEF element of each biological system information and generates an option value for providing at least one biological system information having a similarity index that is equal to or greater than a threshold value if the retrieval query describes any one of the current state and the expected result.

the retrieval requesting unit may assess a similarity between the token of the corpus data set and a term indexed to the PPH element of each biological system information and generates an option value for providing biological system information having a similarity index that is equal to or greater than a threshold value if the retrieval query describes all of the current state and the expected result.

The option value may allow the information management device to assess a similarity between a noun token included in the first corpus data set and a term indexed to the PPH element and a similarity between a verb token included in the second corpus data set and a term indexed to the PPH element.

The retrieval requesting unit may generate an option value for the information management device to perform a similarity assessment with further consideration for a term indexed to the Organ element, the Part element and the Entity element of each biological system information if the term registered in a biological word dictionary exists among tokens of the corpus data set.

The retrieval requesting unit may generate an option value for the information management device to perform a similarity assessment with further consideration for a term indexed to the CoS element of each biological system information if the term registered in a biological word dictionary exists among tokens of the corpus data set.

The biological system information retrieval system may further include a causal model canvas unit, configured for generating and outputting network graphs for each of a predetermined number of similar biological system information that the information management device provides as a result of the similarity assessment according to the corpus data set and the option value. The network graphs may be displayed to include a term indexed to each node constituting similar biological system information and a predetermined number of thumbnail images corresponding to other biological system information that is assessed to have a derivativity for each node.

The derivativity for a node that is the CoS element may be measured with consideration for a similarity index assessment value that respectively compares an adjective set, a noun set of pre condition and a noun set of post condition that are reconfigured terms indexed to the CoS element of similar biological system information to an adjective set, a noun set of pre condition and a noun set of post condition that are reconfigured terms indexed to the CoS element of the biological system information stored in the information management device.

The derivativity for node that is the PPH element or the EPH element may be measured by dividing terms indexed to corresponding element of similar biological system information into a verb part and a noun part respectively, dividing terms indexed to corresponding element of the biological system information stored in the information management device into a verb part and a noun part respectively, and calculating a similarity index assessment value respectively in a semantic distance calculation scheme.

The derivativity for node that is the PEF element, the EBH element, or the Organ element may be measured by calculating a similarity index assessment value based on whether a term indexed to corresponding element of similar biological system information corresponds to a term indexed to corresponding element of the biological system information stored in the information management device.

The derivativity for node that is the Input element may be measured by calculating a similarity index assessment value for a term indexed to Input element of similar biological system information and a term indexed to the Input element of the biological system information stored in the information management device in a semantic distance calculation scheme.

The derivativity for node that is the Entity element may be measured by a semantic distance calculation scheme based on a hierarchical tree data structure between ITIS unique ID indexed to Entity element of similar biological system information and ITIS unique ID indexed to the Entity element of the biological system information stored in the information management device If one of thumbnail images is clicked, the causal model canvas unit may be configured for generating and outputting a network graph according to biological system information corresponding to click thumbnail image.

According to another aspect of the present invention, a method of biological system information retrieval is provided. The method may include receiving input of a retrieval query being described to have at least one of a current state and an expected result, extracting a token for the current state and the expected result from the retrieval query to generate at least one of a first corpus data set for the current state and a second corpus data set for the expected result by using the token, inputting at least one of the first corpus data set and the second corpus data set and an option value being generated according to a predetermined syntax to an information management device, receiving a predetermined number of similar biological system information as a result of a similarity assessment according to the corpus data set and the option value from the information management device, and generating and outputting network graphs for each of the predetermined number of similar biological system information. The information management device may generate, store and manage the biological system information that is specified by physical relations, ecological relations, and biological relations for each organism. The biological system information may be structured information in which nodes are indexed respectively with at least one term according to a predetermined syntax, wherein the nodes are CoS (Change of State) element, PPH (Physical Phenomena) element, PEF (Physical Effects) element, Input element, EPH (Ecological Phenomena) element, EBH (Ecological Behavior) element, Organ element, Part element, Entity element, and Action element. The network graphs may be displayed to include a term indexed to each node constituting similar biological system information and a predetermined number of thumbnail images corresponding to other biological system information that is assessed to have a derivativity for each node.

Any other aspects, features, and advantages will be more clearly understood from the following detailed description taken in conjunction with the accompanying drawings and claims.

According to embodiments of the present invention, it is advantageous for a designer in bio-inspired design to conduct an effective retrieval by using various information and conditions, and to help the designer design inventively by implementing biological system information, which is subject of mimicking and applying in bio-inspired design, including physical relations, ecological relations and/or biological relations, as a comprehensive causal model, and constructing it by ontology.

In addition, compared to conventional approach with which can restrictively retrieval by use a biological entity name (e.g., scientific name or common name) or an associated structure (e.g., gene, disease entity), it is advantageous to retrieve and apply comprehensive or ecological information related to an organism.

DETAILED DESCRIPTION

The invention can be modified in various forms and specific embodiments will be described below and illustrated with accompanying drawings. However, the embodiments are not intended to limit the invention, but it should be understood that the invention includes all modifications, equivalents, and replacements belonging to the concept and the technical scope of the invention.

The terms used in the following description are intended to merely describe specific embodiments, but not intended to limit the invention. An expression of the singular number includes an expression of the plural number, so long as it is clearly read differently. The terms such as "include" and "have" are intended to indicate that features, numbers, steps, operations, elements, components, or combinations thereof used in the following description exist and it should thus be understood that the possibility of existence or addition of one or more other different features, numbers, steps, operations, elements, components, or combinations thereof is not excluded.

Terms such as first, second, etc., may be used to refer to various elements, but, these element should not be limited due to these terms. These terms will be used to distinguish one element from another element.

Terms such as ~part; ~unit, ~module mean an element configured for performing a function or an operation. This can be implemented in hardware, software or combination thereof.

In describing the invention with reference to the accompanying drawings, like elements are referenced by like reference numerals or signs regardless of the drawing numbers and description thereof is not repeated. When it is determined that detailed description of known techniques involved in the invention makes the gist of the invention obscure, the detailed description thereof will not be made.

Figure 1:
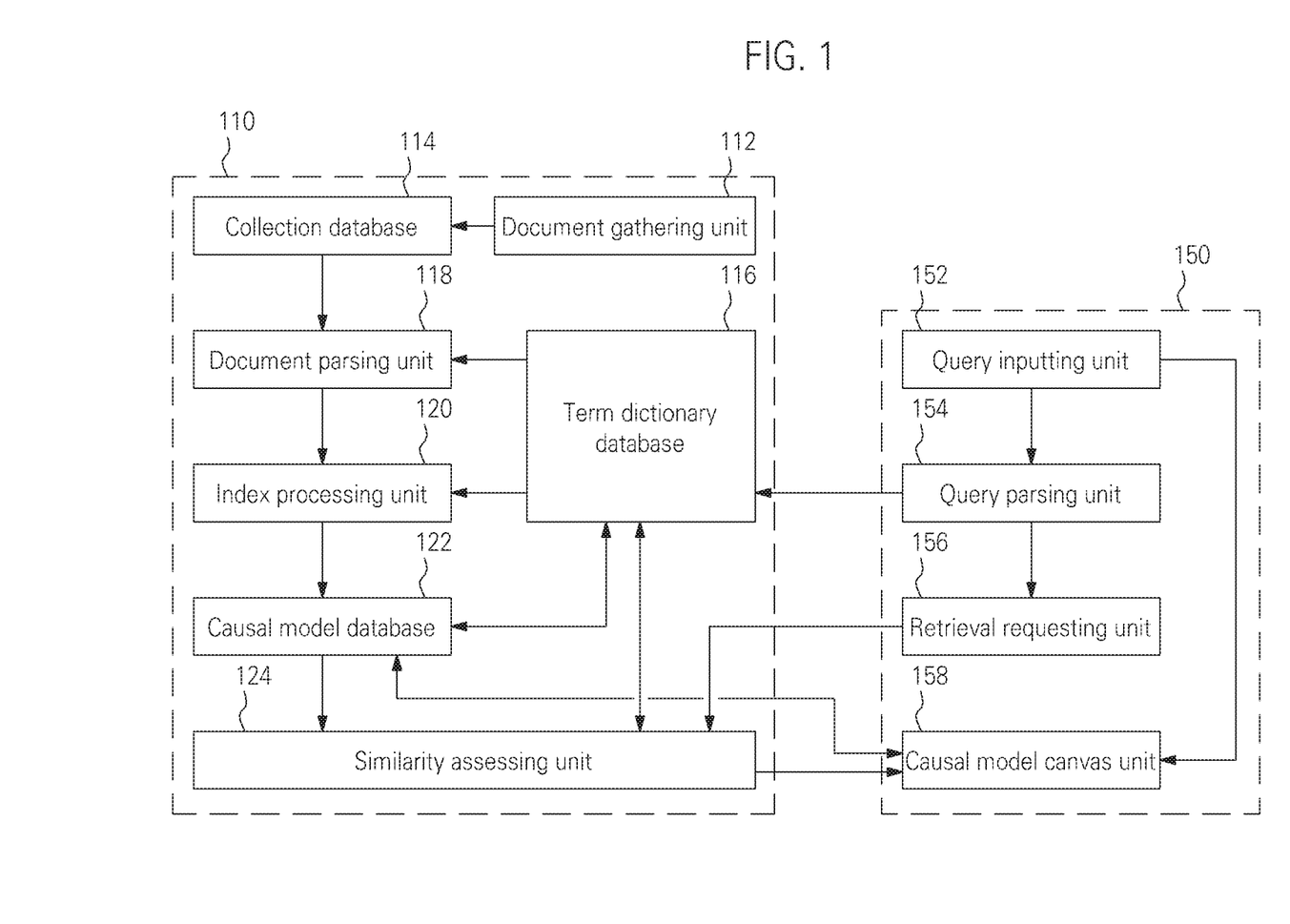
FIG. 1 is a block diagram schematically showing a biological system information retrieval system according to one embodiment of the present invention.
Figure 2:
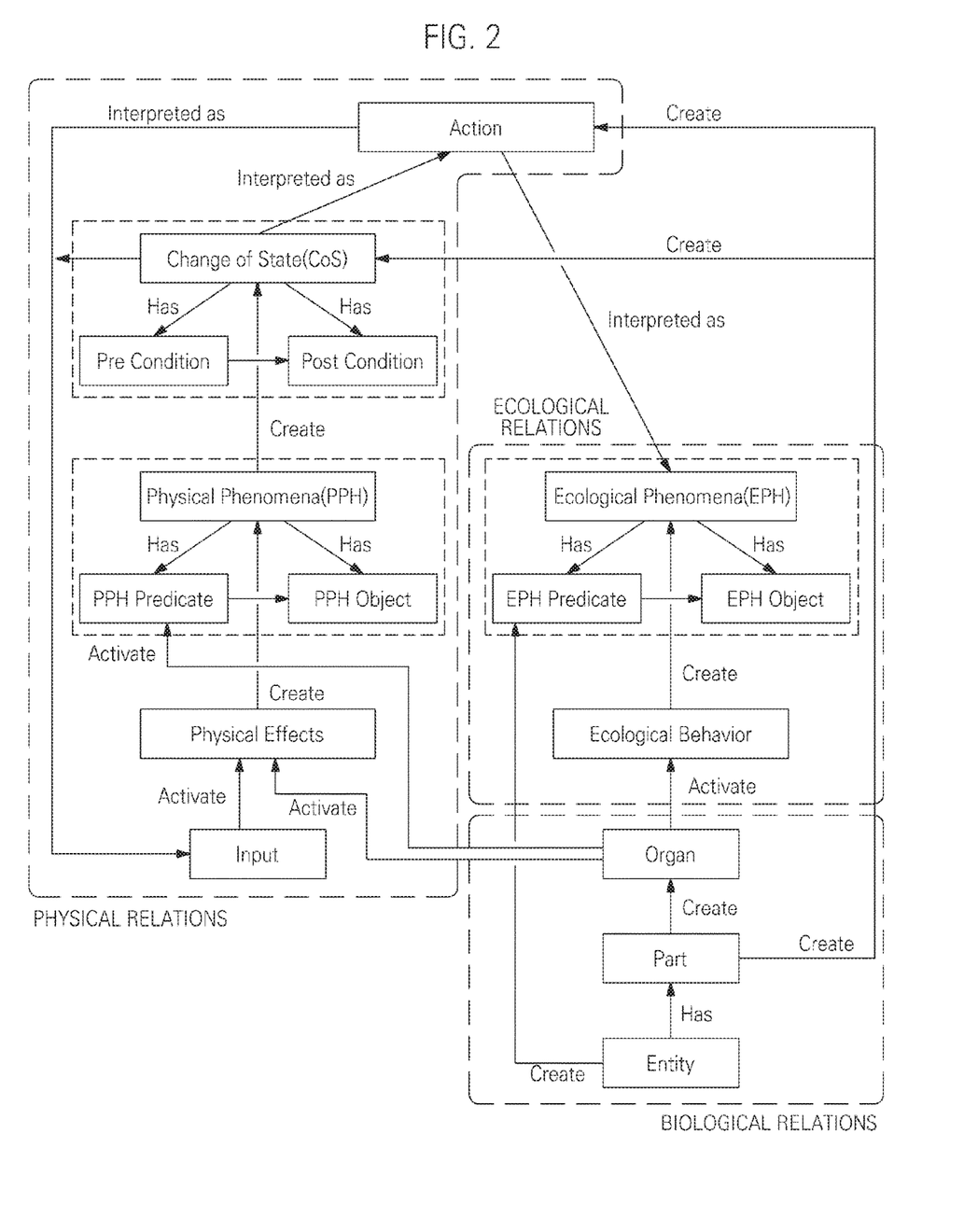
FIG. 2 illustrates an ontology structure based on a causality for constructing a biological system information retrieval system according to one embodiment of the present invention.
Figure 3:
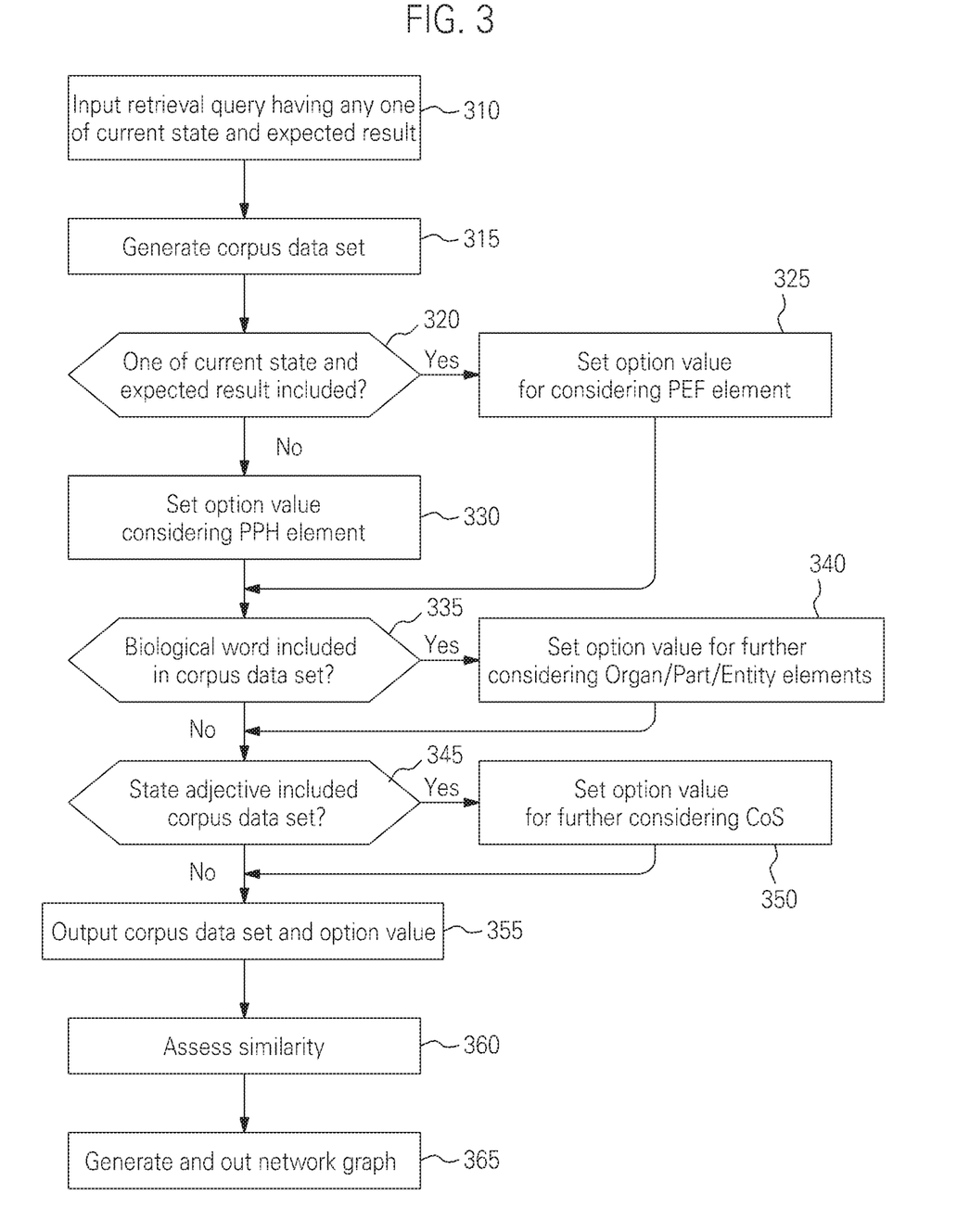
FIG. 3 is a flowchart of reconfiguring a retrieval query according to one embodiment of the present invention.
Figure 4A:
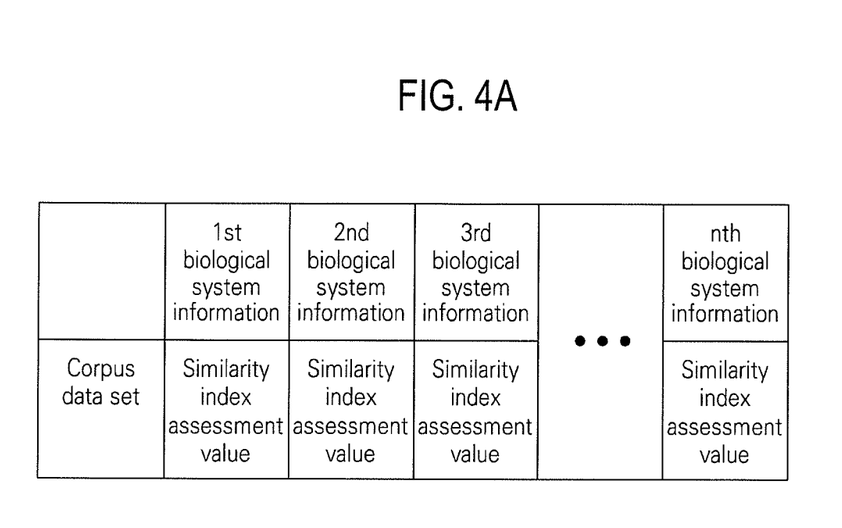
FIGS. 4A and 4B illustrates a similarity matrix and a sub-similarity matrix according to one embodiment of the present invention.
Figure 4B:
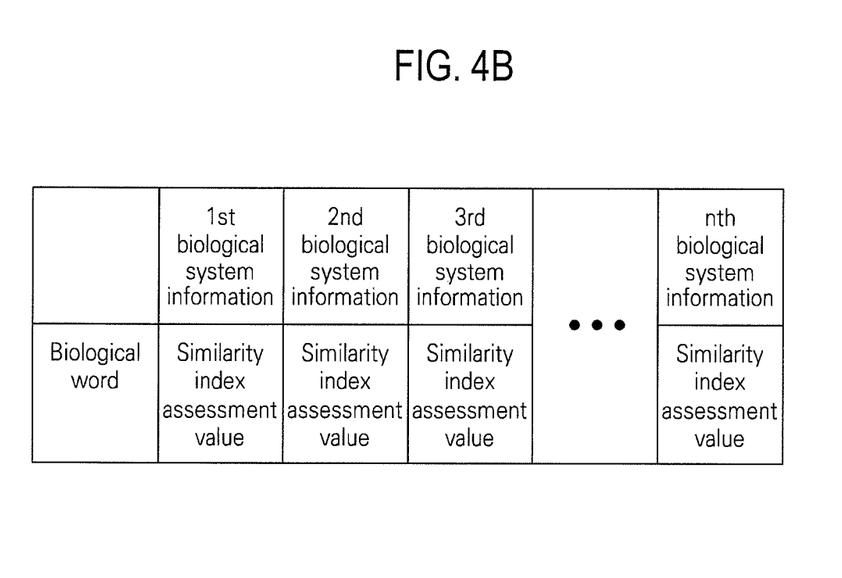
Figure 5:
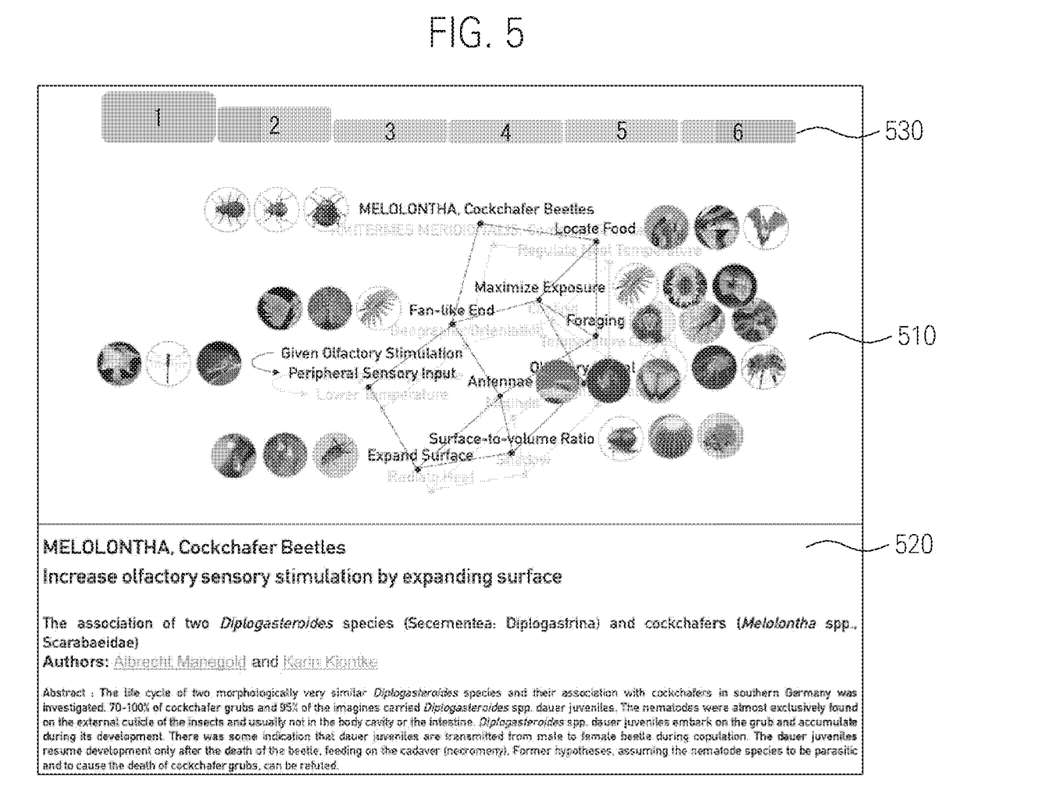
FIG. 5 illustrates a network graph that a causal model canvas unit schematizes according to one embodiment of the present invention.

FIG. 1 is a block diagram schematically showing a biological system information retrieval system according to one embodiment of the present invention, FIG. 2 illustrates an ontology structure based on a causality for constructing a biological system information retrieval system according to one embodiment of the present invention, FIG. 3 is a flowchart of reconfiguring a retrieval query according to one embodiment of the present invention, FIGS. 4A and 4B illustrates a similarity matrix and a sub-similarity matrix according to one embodiment of the present invention, and FIG. 5 illustrates a network graph that a causal model canvas unit schematizes according to one embodiment of the present invention.

Referring to FIG. 1, the biological system information retrieval system may include an information management device 110 and an information using device 150.

Although FIG. 1 illustrates that the information management device 110 and the information using device 150 are independent from each other and connected via wired or wireless communication, it will be appreciated that the information management device 110 and the information using device 150 can be integrated into one device if needed.

The information management device 110 is configured for constructing biological system information that can be a base for a bio-inspired design.

Biological System information specifies physical phenomena, biochemical phenomena and so on in an individual organism that is a subject of mimicking and application as physical relations, ecological relations, and biological relations. Biological System information can be extended an interaction between entities or an interaction between a plurality of species.

In other words, as it could be possible that one organism is directly mimicked but also possible that biological phenomena in organism, interaction(s) made by several entities, or interaction(s) made by various species of organisms are utilized directly or indirectly, biological system information can encompass biological phenomena in individual organism or interactions between organisms or species in order for designers to conceive various ideas in wider range.

For example, if biological information about European-starling having an enzyme that can catalyze alcohol decomposition for alcohol detoxification is stored and managed, a designer who is trying to develop a product for catalyzing alcohol decomposition can access the information management device 110 by using the information using device 150, and can retrieve and utilize information about European-starling by searching biological system information about catalyzing alcohol decomposition.

The information management device 110 may include a document gathering unit 112, a collection database 114, a term dictionary database 116, a document parsing unit 118, an index processing unit 120, a causal model database 122, and a similarity assessing unit 124.

The document gathering unit 112 collects BS (Biological structure) documents constituting of natural language. BS documents may be, for example, natural-language based HTML document arranged by biologists. Of course, author or type of BS documents should not be limited to the aforementioned, but any documents available for categorizing physical relations, ecological relations, and/or biological relations, and creating a causal model would be enough.

The collection database 114 stores BS documents that the document gathering unit 112 collected.

In the term dictionary database 116, terms that are needed to index physical relations, ecological relations, and/or biological relations, which are included in biological system information.

In the term dictionary database 116, a scientific name dictionary in which scientific name terms, for example, according to ITIS (International Taxonomy Information Systems) standard, references quoted in STONE's paper publically published in 2014, and so on may be included as index terms. By using scientific name terms, it would be advantageous for the present invention that can collect biological system information about 21,000 genera based on ITIS.

In addition, since function, material, energy, and/or signal terms are needed to index physical relations and ecological relations respectively, a function term dictionary, a material term dictionary (e.g., Material>Liquid>acid, chemical, water, blood, etc.), energy term dictionary (e.g., Energy>Hydralic>pressure, osmosis etc.), and/or signal term dictionary (e.g., Signal>Sense>Detect>detect, locate, see/Signal>Status>change, fatty, variation, etc.), which are edited by experts, may be stored in the term dictionary database 116. Terms related to EPH (Ecological Phenomena) may be composed of data defining classification relation according to each category of function, material, energy, and/or signal.

The document parsing unit 118 parses BS documents collected by the document gathering unit 112 to analyze a sentence structure of BS documents and to construct the sentence as a tree. The document parsing unit 118 may use a Scrapy parsing unit.

The index processing unit 120 indexes information that the document parsing unit 118 analyzed according to an ontology structure (see FIG. 2) which represents a biological system based on causality in which the conventional SAP-PhIRE model is complemented.

That is, for information analyzed by the document parsing unit 118, the index processing unit 120 indexes biological relations of individual organism based on scientific name terms stored in the term dictionary database 116, and indexes each of physical relations and ecological relations among biological system of the organism based on terms representing function, material, energy, and/or signal respectively.

Biological System information may be derived from a triple form of subject-predicate-object, but, as shown in FIG. 2, may be structured to combine physical relations, ecological relations and/or biological relations that represent a mechanism of the organism and a causality manifested through the mechanism.

The smallest unit for indexing organism based on information analyzed from the collected BS documents is node, and connection information of each node forms relationship information.

Referring to FIG. 2, in physical relations of biological system information, Input (e.g., energy, signal, and/or material input) may activate PEF (Physical Effects), PEF may create PPH (Physical Phenomena), PPH may create CoS (Change of State), and CoS may be interpreted as Action.

Physical relations is information representing in a causality way that one organism undergoes a certain CoS and what causes a certain PPH through a certain PEF to achieve a certain objective (Action, Goal).

In detail, CoS relates to how a state is changed between before achieving the objective and final result, and a static state of pre condition and post condition may be indexed in a dynamic relationship.

PEF relates to a strategy used to achieve the objective, and may be generally indexed as strategies that are contained in an ecology dictionary, a physics dictionary, etc., to have definitions (i.e., definition corresponding to the word).

PPH relates to how a strategy is specifically implemented, and may be indexed with a combination of verb and object that are terms defined in a function term dictionary (verb), and an energy dictionary, a material dictionary, and/or signal dictionary (noun as object), which were edited by experts to represent how it is specifically implemented.

For example, if the European starling detoxifies alcohol, an alcohol detoxification may correspond to Action, CoS may be a change from high concentration of alcohol to low concentration of alcohol, and an alcoholism treatment may be PEF. Thus, Action, that is, objective can be achieved with an alcohol decomposition as PPH.

Specifically, Input such as 'many alcohol molecules' may activate PEF such as 'alcoholism treatment', 'alcoholism treatment' may create PPH such as 'catalyzing alcohol decomposition', as 'catalyzing alcohol decomposition' may create CoS causing 'high concentration of alcohol' (i.e., pre condition) to be changed to 'low concentration of alcohol' (i.e, post condition), and finally this CoS may be interpreted as Action such as 'alcohol detoxification'. Also from an analytical point of view, Action of 'alcohol detoxification' may be reinterpreted as a cause such as Input of 'many alcohol molecules'.

In addition, Action may be interpreted as EPH, so Action can be understood as a physical 'strategy' that an organism will take to do a certain behavior (or habit).

For example, if a designer who wants to develop an alcohol addiction treatment becomes aware of an ecological relation such that European starlings are likely to eat fermented fruits containing alcohol, the designer may infer an ecological relation of alcoholic who needs alcohol detoxification from the ecological relation of European starling, and thus may apply Action of 'alcohol detoxification' that European starling takes as physical strategy to do the behavior (habit) to develop alcoholic treatment as design strategy.

In exemplary case that the collected BS documents contain information about European starling capable of detoxifying alcohol, structured biological system information stored in the term dictionary database 116 can be shown in Table 1 as example. Of course, it will be appreciated that terms stored in correspondence with each node (i.e., Input, PEF, etc.) may be increased and diversified, if European starling has various characteristics.

TABLE 1

| Input | <Alcoholic compound> | <Alcohol> |
|---|---|---|
| Physical Effects | <Alcoholism treatment> | <Alcoholism-treatment> |
| Physical Phenomena | <Catalyze>+<Alcohol decomposition> | <Catalyze> + <Alcohol+Decomposition> |
| Change of State | <High concentration of alcohol> + <Low concentration of alcohol> | <High+Density+of+Alcohol> + <Low+Density+of+Alcohol> |
| Action | <Alcohol detoxification> | <Alcohol+Detoxification> |
| Ecological Phenomena | <Ingest> + <Fermented fruit> | <Ingest> + <Fermented+Fruit> |
| Ecological Behaviors | <Alcohol abuse> | <Alcohol+Abuse> |
| Organ | <Alcohol decomposition enzyme> | <Enzyme> |
| Part | <Stomach> | <Stomach> |
| Entity | <European starling> | <European-starling> + <Sturnus vulgaris> |

In addition, in an exemplary cast that another collected BS documents contain information about European starling having a light skeletal system for reducing air resistance, biological system information about European starling may be additionally generated and managed as shown in Table 2.

TABLE 2

| Input | <Kinetic energy> + <Air resistance> | <Kinetic+Energy> + <Air> |
|---|---|---|
| Physical Effects | <Light weight skeletal system> | <Light-skeletal-system> |
| Physical Phenomena | <Reduce>+<Mass> | <Reduce> + <Body+Weight> |
| Change of State | <High weight> + <Low weight> | <High+Weight> + <Low+Weight> |
| Action | <Reducing energy consumption> | <Reduce+Energy+Consumption> |
| Ecological Phenomena | <Increase> + <Flight time> | <Increase> + <Flight+Time> |
| Ecological Behaviors | <Flight> | <Flying> |
| Organ | <Bone> | <Bone> |

TABLE 2-continued

| Part | <Skeletal system> | <Skeletal-system> |
| Entity | <European starling> | <European-starling> + <*Sturnus vulgaris*> |

Referring to Table 2, biological system information about European starling is that Inputs such as kinetic energy and air resistance may activate PEF such as a light skeletal system, the light skeletal system may generate PPH such as a reduction in bone weight, the reduction in bone weight may create CoS causing a heavy mass to be changed to a light mass, and finally this CoS may be interpreted as Action such as a reduction in energy consumption. Also from an analytical point of view, Action of reduction in energy consumption may be reinterpreted as a cause such as Input of high kinetic energy and air resistance.

In addition, in ecological relations that European starling has a habit of flying efficiently, the designer may regard an ecology of European starling as an ecology of flying object (i.e., in flight), and may apply Action of reduction in energy consumption as a physical strategy that European starling takes to do the behavior to a design strategy for developing a flying object.

As can be seen in FIG. 2 and Tables 1 and 2 respectively, biological relations of biological system information may be consist of Organ, Part, and Entity. Biological relations may indicate that biological phenomena are associated with which organ of an organ in an organism, and Part refers to a part to which the organ belongs.

Entity is an element for indexing that each biological system information is associated with which organism, is the owner of Organ and Part, and is the organism in which the biological phenomena can be observed.

For example, in case of a beetle that produces iridescent color, the beetle may be indexed as Entity, shell may be indexed as Part of biological system since cuticle belongs to shell of beetle, and cuticle of shell may be indexed as Organ.

Referring again FIG. 1, the ontology structure (see FIG. 2) designated by the index processing unit 120 and biological system information that is generated based on terms from each dictionary stored in the term dictionary database 116 are stored in the causal model database 122. Thumbnail images corresponding to each biological system information may be further stored in the causal model database 122.

Hereinafter, a syntax for storing terms for each element in the causal model database 122 will be briefly described.

CoS element may be stored according to a syntax of Expression 1.

$$COS_{Biological\ System} = \{State_{pre}, State_{post}\}$$

$$State_{pre} = \{Adj_{pre}, Noun_{pre}\}$$

$$State_{post} = \{Adj_{post}, Noun_{post}\} \quad \text{Expression 1}$$

CoS may be stored as a pre condition $State_{pre}$ and a post condition, $State_{post}$, and consist of an adjective part Adj and a noun part Noun. In the term dictionary database 116, the adjective part index terms may be stored in a state adjective dictionary, and the noun part index terms may be stored in the material term dictionary, the energy term dictionary, and/or the signal term dictionary respectively.

PPH element may be stored according to a syntax of Expression 2.

$$PPH_{Biological\ System} = \{Predicate_{pre}, Object_{post}\} \quad \text{Expression 2}$$

PPH may consist of a verb part $Predicate_{physical}$ and a noun part ($Object_{physical}$. In the term dictionary database 116, the verb part index terms may be stored in the function term dictionary, and the noun part index terms may be stored in the material term dictionary, the energy term dictionary, and/or the signal term dictionary respectively, as described above.

PEF element may be stored according to a syntax of Expression 3.

$$PEF_{Biological\ System} = \{Index_{physicaleffect}\} \quad \text{Expression 3}$$

PEF may be indexed with one of index terms registered in a PEF index term dictionary stored in the term dictionary database 116. The PEF index term dictionary may be stored in a format of 'index term' and 'definition of index term' (e.g., 'Camouflage'+'Definition of camouflage') in the term dictionary database 116.

Input element may be stored according to a syntax of Expression 4.

$$INP_{Biological\ System} = \{Index_{material}, Index_{energy}, Index_{signal}\} \quad \text{Expression 4}$$

Input that activates biological system information may consist of related material index term $Index_{material}$, energy index term $Index_{energy}$, and/or signal index term $Index_{signal}$. These may be designated from terms registered in the material term dictionary, the energy term dictionary, and/or signal term dictionary stored in the term dictionary database 116.

EPH element may be stored according to a syntax of Expression 5.

$$EPH_{Biological\ System} = \{Predicate_{ecological}, Object_{ecological}\} \quad \text{Expression 5}$$

EPH may consist of a verb part Predicate about 'How' and a noun part Object about 'What'. For example, biological phenomena (camouflage) that cause an illusion to prevent from being detected by an enemy may have a biological function of avoiding enemy (body material). Index terms of the verb part and the noun part may be stored in advance stored in the term dictionary database 116 as the function term dictionary, the material term dictionary, the energy term dictionary, and/or signal term dictionary.

EBH (Ecological Behavior) element may be stored according to a syntax of Expression 6.

$$EBH_{Biological\ System} = \{Index_{ecologicaleffect}\} \quad \text{Expression 6}$$

EBH element may be indexed with one of index terms registered in EBH index term dictionary stored in the term dictionary database 116. For example, the biological phenomena that cause an illusion of foe to prevent from being detected has a biological behavior such as camouflage. Index term dictionary may be stored in a format of 'index term' and 'definition of index term' (e.g., 'Herbivore'+'Definition of herbivore') in the term dictionary database 116.

Organ element and Part element may be stored respectively according to a syntax of Expression 7.

$$ORG_{Biological\ System}=(String_{organ})$$

$$PRT_{Biological\ System}=(String_{part}) \quad \text{Expression 7}$$

Organ element and Part element may be indexed with terms in a biological word dictionary stored in the term dictionary database 116.

Entity element for indexing that biological system information is associated with which organism may be stored according to a syntax of Expression 8.

$$ENT_{Biological\ System}=(ID_{ITIS}, Index_{scientificname}, Index_{common\ name}) \quad \text{Expression 8}$$

In order to make an association search possible. Entity may be indexed by a scientific name according to ITIS system, and $ID_{ITIS}$ may index unique ID (number) of organism, $Index_{scientificname}*(c)$ may index scientific name (text), and $Index_{commonname}$ may index a common name (text) from 'ITIS scientific name dictionary'. ITIS scientific name dictionary for indexation may be stored in the term dictionary database 116.

Action element may be stored respectively according to a syntax of Expression 9.

$$ACT_{Biological\ System}=(String_{action}) \quad \text{Expression 9}$$

Action element may be not stored in a dictionary, and indexed with a description summarized from a design strategy that a designer can obtain from biological system information.

As described above, since biological system information may be represented and respectively indexed with causal model in which physical relations, ecological relations and/or biological relations in each organism have mutual connections (directionality), it is advantageous for a designer to retrieve biological system information that is useful to his idea.

The similarity assessing unit 124 may receive the retrieval query from the retrieval requesting unit 156, may assess similarity between the retrieval query and each biological system information stored in the causal model database 122, and may provide biological system information having similarity equal to or greater than a threshold value to the causal model canvas unit 158. The similarity assessing unit 124 may manage biological system information store in the causal model database 122, for example, in Python language.

Detailed operations of the similarity assessing unit 124 will be described in connection with the retrieval requesting unit 156 and the causal model canvas unit 158 of the information using device 150.

The information using device 150 is configured for retrieving biological system information stored in the information management device 110 and receiving retrieval result, and may include a query inputting unit 152, a query parsing unit 154, a retrieval requesting unit 156, and the causal model canvas unit 158.

The query inputting unit 152 is a means for retrieving biological system information to which a designer may input a retrieval query corresponding to his needs (see 310 in FIG. 3).

The retrieval query may be in various forms including at least one word such as phrase, sentence, or paragraph.

However, in the present embodiment, the retrieval query may consist of natural-language phrase, and may be, for example, described by a combination of <Current state> and <Expected result>.

For this, although it is possible that the query inputting unit 152 may allow to describe <Current state> and <Expected result> in natural-language phrase in one query input slot (e.g., input window for search words), it is also possible to implement such that the query inputting unit 152 may provide the first query input slot for inputting <Current state> in natural-language phrase and the second query input slot for inputting <Expected result> in natural-language phrase, respectively.

In case that the retrieval query is described in a combination of <Current state> and <Expected result>, it will be advantageous that the causality will be more clarified when conducting retrieval, and it will be also effective because biological system information according to the present embodiment adopts a causal model that is expressed in a homogeneous structure.

The query parsing unit 154 may decompose the query phrase inputted by a designer with use of the query inputting unit 152 into tokens, which are words at meaningful level that are processed by a conventional natural language processing method, and analyze grammatical components of each token (e.g., adjective, verb, noun, etc.). In addition, the query parsing unit 154 may refer to terms stored in the term dictionary database 116 of the information management device 110 to generate corpus data set of tokens with query phrases of <Current state> and <Expected result> (See 315 in FIG. 3).

For example, if a designer may input 'the blood alcohol level is very high' as retrieval query for <Current state> and 'the blood alcohol level is normal' as retrieval query for <Expected result> in order to obtain an idea for developing alcoholism treatment, the query parsing unit 154 may generate [blood, alcohol, level, very, high] as a corpus data set for <Current state> and [blood, alcohol, level, normal] as a corpus data set for <Expected result>.

As described above, the corpus data set may be represented in form of a list by tokenizing words and eliminating sentence symbols and stopwords (e.g., a, an, for, and, eta).

The retrieval requesting unit 156 may confirm whether the corpus data set that is inputted by use of the query inputting unit 152 and analyzed by the query parsing unit 154 exists for <Current state> and <Expected result>, and provide corpus data set to which a corresponding option value is added to the similarity assessing unit 124.

Even in case that corpus data set corresponding to the retrieval query to be provided to the similarity assessing unit 124 includes any one of <Current state> and <Expected result>, the similarity assessing unit 124 may be implemented to conduct a retrieval of biological system information and perform a similarity decision. Of course, in case that no corpus data set for <Current state> and <Expected result> exists, this means that no retrieval query is inputted so the following retrieval process will not be performed.

This is because that the bio-inspired design basically assumes a design thinking based on an inference strategy. Thus, a designer may not specify <Expected result> for the purpose of checking various results available under <Current state> condition in order to find idea out, and also may not specify <Current state> for the purpose of checking various pre conditions available under <Expected result>.

Namely, not specifying any one of <Current state> and <Expected result> may be interpreted as an intention not to put a limitation on thinking, and this is a way of design thinking that help a designer infer inventively.

For example, in case that a causality is specifically fixed by associating <Current state> of 'high concentration of alcohol' with <Expected result> of 'low concentration of alcohol', result such as 'high concentration of alcohol' is maintained, but biological system information about Pelotomaculum Thermopropionicum that uses alcohol as an energy source cannot be retrieved.

The operation of the retrieval requesting unit 156 will be described in detail. In case that any one of <Current state> and <Expected result> is specified in the retrieval query, the retrieval requesting unit 156 may utilize PEF element that represents CoS most abstractly among ontology structure of biological system information to set an option value that allows the similarity assessing unit 124 to assess a similarity between information indexed with PEF element of biological system informations stored in the causal model database 122 and corpus data set of the retrieval query, also to draw a similarity matrix, and to provide biological system informations that are equal to or greater than a threshold value to the causal model canvas unit 158 (See 320 and 325 in FIG. 3).

However, in case that both <Current state> and <Expected result> are described in the retrieval query, the retrieval requesting unit 156 may utilize PPH among ontology structure of biological system information to set an option value that allows the similarity assessing unit 124 to assess a similarity between information indexed with PPH element of biological system informations stored in the causal model database 122 and corpus data set of the retrieval query, also to draw a similarity matrix, and to provide biological system informations that are equal to or greater than a threshold value to the causal model canvas unit 158 (See 320 and 330 in FIG. 3).

In detail, since <Expected result> shows an expected behavior as result of change, <Expected result> may allow the similarity assessing unit 124 to collect verb tokes from corpus data set of <Expected result> and to assess similarity between each information indexed as PPH elements. On the other hand, since <Current state> shows a target to be changed, <Current state> may allow the allow the similarity assessing unit 124 to collect noun tokes from corpus data set of <Expected result> and to assess similarity between each information indexed as PPH elements.

By aggregating the calculation result of the similarity assessing unit 124 for verb tokens of <Expected result> and the calculation result of the similarity assessing unit 124 for noun tokens of <Current state>, the similarity assessing unit 124 may draw the similarity matrix and provide biological system informations that are equal to or greater than the threshold value to the causal model canvas unit 158.

In addition, if a term registered in the biological word dictionary stored in the retrieval requesting unit 156 is found, the retrieval requesting unit 156 may set an option value that allows the similarity assessing unit 124 to further consider Organ, Part and Entity elements among the ontology structure of biological system information when assessing the similarity and also to use similarity assessment result when drawing the similarity matrix (See 335 and 340 in FIG. 3).

Here, a biological word relates to an organ, a part and/or an entity name (e.g., common name, scientific name, etc.) of an organism such as sensory-organ, lung, European starling.

But, if a term registered in the biological word dictionary stored is not found, the retrieval requesting unit 156 may set an option value that allows the similarity assessing unit 124 not to consider Organ, Part and Entity elements when assessing the similarity.

In addition, if a term registered in the state adjective dictionary stored in the retrieval requesting unit 156 is found, the retrieval requesting unit 156 may set an option value that allows the similarity assessing unit 124 to further consider CoS elements among the ontology structure of biological system information when assessing the similarity and also to use similarity assessment result when drawing the similarity matrix (See 345 and 350 in FIG. 3)

Here, a state adjective relates to size, shape, state, color, age, material, etc., among adjectives such as high, small, enormous, round, ceramic, metal, and so on.

But, if a term registered in the state adjective dictionary stored is not found, the retrieval requesting unit 156 may set an option value that allows the similarity assessing unit 124 not to consider CoS element when assessing the similarity.

The retrieval requesting unit 156 may provide the similarity assessing unit 124 with corpus data set and option value that are generated according to the inputted retrieval query to request the retrieval (See 355 in FIG. 3).

The causal model canvas unit 158 may measure a derivativity (i.e., interrelationship) between at least one biological system information provided as a similarity index assessment result from the similarity assessing unit 124, and generate a network graph (see FIG. 5) by use of the measure derivativity (See 355 and 360 in FIG. 3). Of course, it will be appreciated that the similarity assessing unit 124 may measure the derivativity and the causal model canvas unit 158 may generate the network graph by use of the result of derivativity measurement.

Hereinafter, it will be described that the similarity assessing unit 124 conducts the retrieval by use of corpus data set corresponding to the retrieval query that the retrieval requesting unit 156 provides and biological system information about each organism stored in the causal model database 122, and assesses the similarity (See 355 in FIG. 3).

In order to perform the similarity assessment on biological system information stored in the causal model database 122 and corpus data set of <Current state> and/or <Expected result>, in case that n biological system informations are stored in the causal model database 122, the similarity assessing unit 124 may generate a 1×n similarity matrix for comparison with corpus data set (See in FIG. 4A). Each similarity index assessment value may be initialized to zero before performing the similarity assessment.

In case that corpus data set for any one of <Current state> and <Expected result> corresponding to the retrieval query is provided, the similarity assessing unit 124 may calculate a degree of topic interrelationship between the corpus data set and definition text (stored in PEF index term dictionary) for each of n biological system informations stored in the causal model database 122 by use of tf-idf (Term Frequency-Inverse Document Frequency) scheme,) store the calculated value as similarity index assessment values of each biological information. If similarity value that was calculated already in previous similarity index assessment process exists, they will be summed.

Tf-idf scheme is a conventional scheme for comparing similarity between two documents with similarity of terms (tokens) used in each document. For example, in case that corpus data consists of [blood, alcohol, level, very, high], Tf-idf scheme compares the number of appearances in documents about 'Alcoholism-treatment' that is definition text of index term of PEF element with the number of appearances in definition documents for all terms in PEF index term dictionary. Since tokens such as level, very, high, etc. are frequently used in most of documents, it will be appreciated that relatively low similarity index value may be assigned to these tokens compared to other tokens such as blood, alcohol, etc.

But, in case that only corpus data set for both <Current state> and <Expected result> is provided, the similarity assessing unit 124 may generate a verb token set Wp by extracting verb tokens from corpus data set $W_{ER}$ of <Expected result> and a noun token set Wo by extracting noun tokens from corpus data set $W_{CS}$ of <Current state> by use of a conventional POST (Part of speech tagging) algorithm and so on.

For example; in case that corpus data set of <Current state> consists of [blood, alcohol, level, very, high]; since there is no token that can be considered as verb, verb token set Wp will be empty, but the noun token set Wo will be generated as [blood, alcohol, level].

The similarity assessing unit 124 may generate the first similarity index calculation value by calculating similarity index between terms in the verb token set and verb part (Predicate$_{physical}$, see Expression 2) of PPH element of each biological system information. In addition, the similarity assessing unit 124 may generate the second similarity index calculation value by calculating similarity index between terms in the noun token set and noun part (Object$_{physical}$) of PPH element of each biological system information, and store multiplication of the first and the second similarity index calculation values as similarity index assessment value for each biological system information. If similarity index assessment value that was calculated already in previous similarity index assessment process (e.g., similarity index assessment based on the presence/absence of biological word) exists, they will be summed.

In above example, since the verb token set Wp is empty, the first similarity index calculation value will be zero. But, in case that the verb token set Wp is not empty and PPH element of a certain biological system information is indexed as <Adjust>+<Direction+of+Incident+Light>, the similarity index between the verb token in the verb token set Wp and <Adjust> as verb part of PPH element will be calculated.

As described above, since verb terms are registered in the function term dictionary stored in the causal model database 122, the first similarity index calculation value may be generated by calculating a semantic distance between the verb token of the verb token set Wp and Adjust.

The function term dictionary may be composed of a tree data structure to calculate semantic distance between each term. The first similarity index calculation value may be generated as a distance that verb token reaches Adjust via a parent node that is common and nearest from both verb token and Adjust (i.e., the number of edges connecting each hierarchical node). Thus, as farther the nearest parent node is away from the highest node, as higher the first similarity value will be. This type of tree data structure may be structured in similar manner to a hierarchical structure having a connection relationship between nodes so as to calculate the degree of kinship.

In addition, in case that the noun token set Wo is not empty and PPH element of a certain biological system information is indexed as <Adjust>+<Direction+of+Incident+Light>, similarity index between noun token of the noun token set Wo and 'Direction' and 'Light' as noun part of PPH element may be calculated. The second similarity index calculation value may also be calculated by use of semantic distance of term in same manner as the process of the first similarity index calculation value, and if nouns to be calculated are plural (e.g., 'Direction' and 'Light'), for example, an average, a sum, or a maximum value of these may be calculated as the second similarity index calculation value.

Then, the similarity assessing unit 124 may check whether the state adjective (e.g., small, high, etc.) exists in corpus data set corresponding to the retrieval query, and if exists, further perform similarity index assessment in consideration with the state adjective.

In case that the state adjective is found in corpus data set of <Current state> and/or <Expected result>, all multiplication of frequencies found in adjective part (See Expression 1) among index information of CoS element of each biological system information stored in the causal model database 122 may be stored as similarity index assessment value for each biological system information. If similarity index assessment value that was calculated already in previous similarity index assessment process exists, they will be summed. The state adjective of corpus data set of <Current state> may be compared to adjective part Adj$_p$re of pre condition and the state adjective of corpus data set of <Expected result> may be compared to adjective part Adj$_{post}$ of post condition, and if an adjective is found both in corpus data sets of <Current state> and <Expected result>, a multiplication of each frequency may be stored as the similarity index assessment value.

For example, in case that CoS element of a certain biological system information consists of <High+Weight> and <Low+Weight>, the adjective part of pre condition is 'High' and the adjective part of post condition is 'Low'. Assuming that state adjective of corpus data set of <Current state> is 'High, Small' and the state adjective of corpus data set of <Expected result> is 'Normal', 'High' is found once but 'small' is not found in state adjectives of <Current state> so the multiplication of frequencies is zero, and the frequency for state adjective of <Expected result> is zero. Thus, the similarity index assessment value is zero.

As described above, by using a mechanism of multiplying frequencies, in case that all elements are found, it can be used as an additional point to the similarity index assessment value.

In addition, as shown in of FIG. 4B, if corpus data set has a biological word, the similarity assessing unit 124 may further generate a 1×n sub similarity matrix.

For example, in case that corpus data set of <Current state> is [blood, alcohol, level, very, high] and corpus data set of <Expected result> is [blood, alcohol, level, normal], token such as 'blood' is a biological word registered in the biological word dictionary. The similarity assessing unit 124 may compare the biological word to each of n biological system informations stored in the causal model database 122. If 'blood' was found twice in indexed terms corresponding to Organ, Part and Entity elements of j$^{th}$ biological system information, the sum of frequencies is two, and two as the similarity index assessment value between j$^{th}$ biological system information and token as the biological word included in corpus data set may be registered as j$^{th}$ element of the sub similarity matrix.

As described above, the similarity assessing unit 124 may generate each of the similarity matrix and the sub similarity matrix by use of corpus data set corresponding to the retrieval query and biological system information for each organism stored in the causal model database 122. The similarity matrix is generated for all of designer's retrieval requests, but the sub similarity matrix is generated only when a biological word is included in corpus data set.

Hereinafter, a process will be described that when the similarity assessing unit 124 provides the causal model canvas unit 158 with at lease one biological system information with reference to the similarity index assessment value generated in the aforementioned process, the causal model canvas unit 158 may measure derivativity between each biological system information, and plot the network graph (See FIG. 5). Of course, it will be appreciated that the similarity assessing unit 124 may measure the derivativity and the causal model canvas unit 158 may generate the network graph by use of the result of derivativity measurement.

After assessing similarity between corpus data set and biological system information of each organism by use of the similarity matrix and/or the sub similarity matrix, the similarity assessing unit 124 may provide the causal model canvas unit 158 with at least one biological system information of which similarity index assessment value is equal to or greater than a threshold value. The threshold value may be, for example, designated as 0.75, which means to provide biological system information corresponding to the upper 75%.

FIG. 5 illustrates the network graph that the causal model canvas unit 158 generates graphically by measuring derivativity of at least one biological system information provided from the similarity assessing unit 124.

Referring to FIG. 5, a graph display screen may be divided into a graph region 510 and an information display region 520.

In the graph region 510, a network graph for biological system information assessed as having high similarity index assessment value is displayed, and numbers in series 530 for allowing a designer to select biological system information in the order of high similarity index assessment values may be disposed in upper region. If the designer changes number 1 to number 2, a network graph for biological system information in group 2 of which similarity index assessment value is relatively low may be displayed in the graph region 510.

For example, as shown in FIG. 5, a network graph corresponding to a group selected by the designer among numbers may be displayed relatively clearly in the graph region 510, but network graphs corresponding to groups not selected may be displayed relatively blurredly in the graph region 510. The designer will be able to expect existences of each network graph corresponding each number with reference to the clear network graph and the blurred network graphs.

In the graph region 510, at least one thumbnail image corresponding to other biological system information indexed with similar information for each element of biological system information may be displayed. That is, the thumbnail image may correspond to other biological system information having similar information for each element of biological system information displayed in the graph region 510, and have a hyperlink to move to biological system information of the organism when the designer selects any one of thumbnail images.

For example, if biological system information displayed in the graph region 510 relates to a Cockchafer Beetle, three thumbnail images displayed along Entity element indexed with [*Melolontha*, Cockchafer Beetle] relate to other three biological system information of which Entity element is indexed with information similar to Cockchafer Beetle.

In the information display region 520, biological system information that is displayed as network graph in the graph region 510 and/or related BS documents are displayed in text.

Hereinafter, a method that the causal model canvas unit 158 measures derivativity for each element of biological system information to further display thumbnail image on the network graph will be described.

The causal model canvas unit 158 may use 1×n similarity matrix in order to measure derivativity with other biological system information by use of information indexed to each element of any one of biological system information.

The similarity matrix for measuring derivativity has a form similar to the similarity matrix described with reference to FIG. 4A, but information to be compared is information indexed to each element of any one of biological system information instead of corpus data set. Thus, in case that same biological system information as index information of element to be compared is compared, the similarity index will be one so this biological system information needs to be excluded from being displayed as thumbnail image.

A scheme of measuring derivativity for CoS element is shown in Expression 10.

$$\text{Adj}:\{\text{Adj}|\text{Adj}_{pre}+\text{Adj}_{post}\}$$

$$t \in S(t_i, t_j)$$

$$sim(t_i, t_j) = \max[-\log(p(t))]$$

if, $a=b$ then, $\text{Boolean}(a,b)=1$ if, $a \neq b$ then, $\text{Boolean}(a,b)=0$ $$\text{Score}_j = sim(\text{Noun}_{pre_i}, \text{Noun}_{pre_j}) + sim(\text{Noun}_{post_i}, \text{Noun}_{post_j}) + \text{Boolean}(\text{Adj}_i, \text{Adj}_j) \quad \text{Expression 10}$$

CoS element may be indexed, for example, as <pre condition>+<post condition> such as <Given+Olfactory+Stimulation>+<Peripheral+Sensory+Input>, and after being reconfigured as adjective set [given, peripheral], noun set of pre condition [olfactory, stimulation], and noun set of post condition [sensory, input], may be compared to index information of CoS element of other biological system information.

In comparison of adjective sets, 1 is outputted if they are matched to each other and 0 is outputted if they are not matched to each other. In the same manner as the comparison of PPH as described above, Noun sets of pre condition and post condition may be calculated in the semantic distance calculation scheme based on the energy term dictionary, the signal term dictionary and/or the material term dictionary, and then the similarity index assessment value may be calculated by summing all of these values.

A scheme of measuring derivativity for PPH element is shown in Expression 11.

$$t \in S(t_i, t_j)$$

$$sim(t_i, t_j) = \max[-\log(p(t))]$$

$$\text{Score}_j = sim(\text{Predicate}_{physical_i}, \text{Predicate}_{physical_j}) + sim(\text{Object}_{physical_i}, \text{Object}_{physical_j}) + \text{Boolean}(\text{Adj}_i, \text{Adj}_j) \quad \text{Expression 11}$$

PPH element may be indexed, for example, as <verb part>+<noun part> such as <Expand>+<Surface>, and when comparing to index term of PPH element of other biological system information, the verb part may be calculated in the semantic distance calculation scheme based on the function term dictionary, and the noun part may be calculated in the semantic distance calculation scheme based on the energy term dictionary, the signal term dictionary and/or the material term dictionary. Each calculation value may be summed to be the similarity index assessment value.

A scheme of measuring derivativity for PEF element is shown in Expression 12.

if, $a=b$ then, Boolean$(a,b)=1$ if, $a \neq b$ then, Boolean$(a,b)=0$ $$Score_j = Boolean(PEF_i, PEF_j) \quad \text{Expression 12}$$

PEF element may be indexed with term such as <Surface-to-Volume Ratio> included in the PEF index term dictionary, and be compared to index term of PEF element of other biological system information. If they are matched to each other, one is outputted, and if they are not matched to each other, zero is outputted. These values may be used as similarity index assessment value.

A scheme of measuring derivativity for Input element is shown in Expression 13.

$t \in S(t_i, t_j)$ $sim(t_i, t_j) = \max[-\log(p(t))]$ $$Score_j = sim(Index_{material_i}, Index_{material_j}) + sim(Index_{energy_i}, Index_{energy_j}) + sim(Index_{signal_i}, Index_{signal_j}) \quad \text{Expression 13}$$

Input element may be indexed with term such as <Olfactory Signal> included in the energy term dictionary, the signal term dictionary or the material term dictionary, and when compared to index term of PPH element of other biological system information, if indexed information such as <Olfactory Signal> corresponds to the signal index term only, the assessment results for the material index term and the signal index term may be outputted as zero. But the similarity index assessment value for the signal index term may be calculated by use of the semantic distance calculation scheme based on the signal term dictionary.

A scheme of measuring derivativity for EPH element is shown in Expression 14.

$t \in S(t_i, t_j)$ $sim(t_i, t_j) = \max[-\log(p(t))]$ $$Score_j = sim(Predicate_{ecological_i}, Predicate_{ecological_j}) \cdot sim(Object_{ecological_i}, Object_{ecological_j}) \quad \text{Expression 14}$$

EPH element may consist of <verb part> and <noun part> such as <Locate>+<Food>, and when comparing to index term of EPH element of other biological system information, verb part may be calculated by use of the semantic distance calculation scheme based on the function term dictionary, and noun part may be calculated by use of the semantic distance calculation scheme based on the energy term dictionary, the signal term dictionary and/or the material term dictionary. Calculation values may be summed to be the similarity index assessment value.

A scheme of measuring derivativity for EBH element is shown in Expression 15.

if, $a=b$ then, Boolean$(a,b)=1$ if, $a \neq b$ then, Boolean$(a,b)=0$ $$Score_j = Boolean(Index_{ecologicaleffect_i}, Index_{ecologicaleffect_j}) \quad \text{Expression 15}$$

EBH element may be indexed with term such as <Foraging> included in the EBH term dictionary, and compared to index term of EBH element of other biological system information. If they are match to each other, one is outputted, and if they are not matched to each other, zero is outputted. These values may be used as the similarity index assessment value.

A scheme of measuring derivativity for each of Organ element and Part element is shown in Expression 16.

if, $a=b$ then, Boolean$(a,b)=1$ if, $a \neq b$ then, Boolean$(a,b)=0$ $$Score_j = Boolean(String_{organ_i}, String_{organ_j}) \quad \text{Expression 16}$$

Organ element and Part element may be indexed with term such as <Fan-like End>, <Antennae> included in the biological term dictionary, and compared to index term of Organ element or Part element of other biological system information. If they are match to each other, one is outputted, and if they are not matched to each other; zero is outputted. These values may be used as the similarity index assessment value.

A scheme of measuring derivativity for Entity element is shown in Expression 17.

$t \in S(t_i, t_j)$ $sim(t_i, t_j) = \max[-\log(p(t))]$ $$Score_j = sim(ID_{ITIS_i}, ID_{ITIS_j}) \quad \text{Expression 17}$$

Entity element may be indexed by including ITIS unique ID (i.e., numeral code for scientific name designated by International standard ITIS), and the similarity index with unique ID of Entity element of other biological system information may be calculated in the same manner of calculating the semantic distance based on a hierarchical tree data structure that unique ID of scientific name has.

A scheme of measuring derivativity for Action element is shown in Expression 18.

if, $a=b$ then, Boolean$(a,b)=1$ if, $a \neq b$ then, Boolean$(a,b)=0$ $$Score_j = Boolean(String_{action_i}, String_{action_j}) \quad \text{Expression 18}$$

Action element may be indexed with a combination of words such as <Maximize Exposure>, and compared to index term of Action element of other biological system information. If they are matched to each other, one is outputted, and if they are not matched to each other, zero is outputted. These values may be used as similarity index assessment value.

By aforementioned schemes, the derivativity for each element of biological system information of which network graph is displayed in the graph region 510 may be calculated, thumbnail images for a predetermined number of other biological system information having high derivativity for each element may be displayed to correspond to each element of biological system information constituting the network graph.

As described above, the biological system information retrieval system according to the present embodiment may implement biological system information, which is subject of mimicking and applying in bio-inspired design, including physical relations, ecological relations and/or biological relations, as a comprehensive causal model, and construct it by ontology. Thus, it is advantageous for a designer in the bio-inspired design to conduct an effective retrieval by using various information and conditions, and to help the designer design inventively.

The method for biological system information retrieval according to embodiment of the present invention may be implemented as computer-readable code on a computer-readable medium. The computer-readable medium may include all types of medium containing data that a computer system can read. In addition, the computer-readable medium may be distributed to computer systems connected to a communication network and store a code that is readable in distributional way.

While the invention has been described above with reference to exemplary embodiments, it will be understood by those skilled in the art that the invention can be modified and changed in various forms without departing from the concept and scope of the invention described in the appended claims.

What is claimed is:

1. A method of retrieving biological system information on a biological system information retrieval system, comprising:
  receiving input of a retrieval query being described to have at least one of a current state and an expected result;
  extracting a token for the current state and the expected result from the retrieval query to generate at least one of a first corpus data set for the current state and a second corpus data set for the expected result by using the token;
  inputting at least one of the first corpus data set and the second corpus data set and an option value being generated according to a predetermined syntax to an information management device;
  receiving a predetermined number of similar biological system information as a result of a similarity assessment according to the corpus data set and the option value from the information management device; and
  generating and outputting network graphs for each of the predetermined number of similar biological system information,
  wherein the information management device generates, stores and manages the biological system information that is specified by physical relations, ecological relations, and biological relations for each organism.

2. The method according to claim 1, wherein the biological system information is structured information in which nodes are indexed respectively with at least one term according to a predetermined syntax, wherein the nodes are CoS (Change of State) element, PPH (Physical Phenomena) element, PEF (Physical Effects) element, Input element, EPH (Ecological Phenomena) element, EBH (Ecological Behavior) element, Organ element, Part element, Entity element, and Action element,
  wherein the network graphs are displayed to include a term indexed to each node constituting similar biological system information and a predetermined number of thumbnail images corresponding to other biological system information that is assessed to have a derivativity for each node.

3. The method according to claim 2, wherein the inputting of at least one of the first corpus data set and the second corpus data set and an option value being generated according to a predetermined syntax to an information management device comprises assessing a similarity between the token of the corpus data set and a term indexed to correspond to the PEF element of each biological system information and generating the option value for providing at least one biological system information having a similarity index that is equal to or greater than a threshold value if the retrieval query describes any one of the current state and the expected result.

4. The method according to claim 2, wherein the inputting of at least one of the first corpus data set and the second corpus data set and an option value being generated according to a predetermined syntax to an information management device comprises assessing a similarity between the token of the corpus data set and a term indexed to the PPH element of each biological system information and generating the option value for providing biological system information having a similarity index that is equal to or greater than a threshold value if the retrieval query describes all of the current state and the expected result.

5. The method according to claim 4, wherein the option value allows the information management device to assess a similarity between a noun token included in the first corpus data set and a term indexed to the PPH element and a similarity between a verb token included in the second corpus data set and a term indexed to the PPH element.

6. The method according to claim 3, wherein the inputting of at least one of the first corpus data set and the second corpus data set and an option value being generated according to a predetermined syntax to an information management device comprises generating the option value for the information management device to perform a similarity assessment with further consideration for a term indexed to the Organ element, the Part element and the Entity element of each biological system information if the indexed term is registered in a biological word dictionary and exists among tokens of the first and the second corpus data set.

7. The method according to claim 3, wherein the inputting at least one of the first corpus data set and the second corpus data set and an option value being generated according to a predetermined syntax to an information management device comprises generating the option value for the information management device to perform a similarity assessment with further consideration for a term indexed to the CoS element of each biological system information if the indexed term is registered in a biological word dictionary and exists among tokens of the first and the second corpus data set.

8. The method according to claim 2, wherein the derivativity for a node that is the CoS element is measured with consideration for a similarity index assessment value that respectively compares an adjective set, a noun set of precondition and a noun set of post condition that are reconfigured terms indexed to the CoS element of similar biological system information to an adjective set, a noun set of pre-condition and a noun set of post condition that are reconfigured terms indexed to the CoS element of the biological system information stored in the information management device.

9. The method according to claim 2, wherein the derivativity for node that is the PPH element or the EPH element is measured by dividing terms indexed to a corresponding element of a similar biological system information into a verb part and a noun part respectively, dividing terms indexed to the corresponding element of the biological system information stored in the information management device into a verb part and a noun part respectively, and calculating a similarity index assessment value respectively in a semantic distance calculation scheme.

10. The method according to claim 2, wherein the derivativity for a node that is the PEF element, the EBH element, or the Organ element is measured by calculating a similarity index assessment value based on whether a term indexed to a corresponding element of a similar biological system information corresponds to a term indexed to the corresponding element of the biological system information stored in the information management device.

11. The method according to claim 2, wherein the derivativity for a node that is the Input element is measured by calculating a similarity index assessment value for a term indexed to Input element of similar biological system information and a term indexed to the Input element of the biological system information stored in the information management device in a semantic distance calculation scheme.

12. The method according to claim 2, wherein the derivativity for a node that is the Entity element is measured by a semantic distance calculation scheme based on a hierarchical tree data structure between ITIS (International Taxonomy Information Systems) unique ID indexed to Entity element of similar biological system information and ITIS unique ID indexed to the Entity element of the biological system information stored in the information management device.

13. The method according to claim 2, wherein if one of thumbnail images is clicked, a network graph according to biological system information corresponding to click thumbnail image is generated and outputted.

14. The method according to claim 3, wherein the inputting of at least one of the first corpus data set and the second corpus data set and an option value being generated according to a predetermined syntax to an information management device comprises generating the option value for the information management device to perform a similarity assessment with further consideration for a term indexed to the Organ element, the Part element and the Entity element of each biological system information if the indexed term is registered in a biological word dictionary and exists among tokens of the first and the second corpus data set.

15. The method according to claim 3, wherein the inputting of at least one of the first corpus data set and the second corpus data set and an option value being generated according to a predetermined syntax to an information management device comprises generating the option value for the information management device to perform a similarity assessment with further consideration for a term indexed to the CoS element of each biological system information if the indexed term is registered in a biological word dictionary and exists among tokens of the first and the second corpus data set.

* * * * *